(12) United States Patent
Togashi et al.

(10) Patent No.: US 7,874,827 B2
(45) Date of Patent: Jan. 25, 2011

(54) SYRINGE MOLD

(75) Inventors: Hiroshi Togashi, Tokyo (JP); Morihiro Sudo, Tokyo (JP)

(73) Assignee: Daikyo Seiko Ltd., Tokyo (JP)

( * ) Notice: Subject to any disclaimer, the term of this patent is extended or adjusted under 35 U.S.C. 154(b) by 204 days.

(21) Appl. No.: 12/310,796

(22) PCT Filed: Sep. 11, 2007

(86) PCT No.: PCT/JP2007/068024

§ 371 (c)(1),
(2), (4) Date: Mar. 6, 2009

(87) PCT Pub. No.: WO2008/032853

PCT Pub. Date: Mar. 20, 2008

(65) Prior Publication Data

US 2009/0232932 A1    Sep. 17, 2009

(30) Foreign Application Priority Data

Sep. 11, 2006    (JP) .............................. 2006-246192

(51) Int. Cl.
*B29C 33/04* (2006.01)
*B29C 33/44* (2006.01)

(52) U.S. Cl. ..................... 425/190; 425/468; 425/577; 425/DIG. 10

(58) Field of Classification Search ................. 425/190, 425/468, 567, 568, 570, 573, 572, 552, 577, 425/581, 588, DIG. 10
See application file for complete search history.

(56) References Cited

U.S. PATENT DOCUMENTS

| | | | | |
|---|---|---|---|---|
| 3,013,308 A | * | 12/1961 | Armour | 29/451 |
| 3,330,004 A | * | 7/1967 | Cloyd et al. | 72/386 |
| 4,919,608 A | * | 4/1990 | Catalanotti et al. | 425/556 |
| 5,009,587 A | * | 4/1991 | Corvaglia et al. | 425/549 |
| 6,077,067 A | * | 6/2000 | Gellert | 425/552 |
| 6,331,174 B1 | * | 12/2001 | Reinhard et al. | 604/232 |
| 6,425,752 B1 | * | 7/2002 | Check | 425/526 |
| 7,143,814 B1 | * | 12/2006 | James | 165/47 |

(Continued)

FOREIGN PATENT DOCUMENTS

JP    S51-067373 A    6/1976

(Continued)

*Primary Examiner*—Yogendra N Gupta
*Assistant Examiner*—Emmanuel S Luk
(74) *Attorney, Agent, or Firm*—Manabu Kanesaka (57) ABSTRACT

A syringe mold with a coolant circulation outward and homeward positioned close to the cavity space and a sufficient coolant circulating flow for cooling a core cylinder is provided.

Slide cores (5, 5) are put in the position where the slide cores (5, 5) protrude from the circumference of the core cylinder (2) by moving the slide core operating jig (4) forward in the axial direction of the core cylinder (2) while cooling the core cylinder (2) by the coolant. Then, a two medical agent mixing type syringe having a communicating groove on the inner circumference for mixing two medical agents is injection-molded. A molding failure due to insufficient cooling of the core cylinder (2) can be prevented by positioning the coolant outward and homeward close to the cavity space and making the cross sectional area of the coolant outward and homeward enough large because the coolant outward and homeward is partitioned by the circumference of the jig container space in the core cylinder (2).

6 Claims, 11 Drawing Sheets

U.S. PATENT DOCUMENTS

| | | | |
|---|---|---|---|
| 7,229,276 B2 * | 6/2007 | Chiba | 425/555 |
| 2001/0015512 A1 * | 8/2001 | Fontana | 264/328.1 |
| 2001/0028930 A1 * | 10/2001 | Koch et al. | 428/35.7 |
| 2002/0003199 A1 * | 1/2002 | Check et al. | 249/79 |

FOREIGN PATENT DOCUMENTS

| | | |
|---|---|---|
| JP | S51-087562 A | 7/1976 |
| JP | S59-136216 A | 8/1984 |
| JP | H04-044816 A | 2/1992 |
| JP | 1995-035021 U | 6/1995 |
| JP | H08-132444 A | 5/1996 |
| JP | 2005-288908 A | 10/2005 |

* cited by examiner

SYRINGE MOLD

TECHNICAL FIELD

The present invention relates to a syringe mold for injection-molding a two medical agent mixing type syringe.

BACKGROUND ART

A communicating groove is injection-molded in an integrated manner on the inner circumference of a two medical agent mixing type syringe for mixing two medical agents contained on the both sides of a piston by circumventing the piston. A conventional syringe mold for a two medical agent mixing type syringe with such a communicating groove formed on the inner circumference is disclosed in Japanese Patent Laid-open Application No. H8-132444.

The syringe mold disclosed in Japanese Patent Laid-open Application No. H8-132444 comprises a cylindrical male die (core cylinder) for molding the inner circumference of the syringe, a slide core for molding the communicating groove which is mounted to move in and out the circumference of the molding male die (core cylinder), and a rotational axis rod incorporated in the molding male die (core cylinder) and coupled to the slide core via a cam mechanism. The slide core moves in and out the circumference of the molding male die (core cylinder) according to the rotation direction of the rotational axis rod.

In this mold, the coolant circulation passage for cooling the molding male die (core cylinder) is formed to penetrate the rotational axis rod, and extends to a molding female die.

There is a molding failure problem due to insufficient cooling of the molding male die (core cylinder) in the conventional mold because it has the cam mechanism for coupling the cam axis to the slide core and the cam mechanism is an obstacle for cooling. The coolant for cooling the molding male die (core cylinder) can flow only in the center portion of the molding male die which is farthest from the molding space where resin is filled. The outer diameter of the flow passage is limited and a sufficient circulating flow cannot be obtained.

DISCLOSURE OF INVENTION

A purpose of the present invention is to provide a syringe mold with a coolant circulating passage and a sufficient coolant circulating flow for cooling a core cylinder.

A syringe mold according to the present invention comprises a core cylinder for forming the inner circumference of a two medical agent mixing type syringe having a communicating groove on the inner circumference for mixing two medical agents, wherein the core cylinder includes a jig container space extending axially, a coolant circulation outward and a coolant circulation homeward which are partitioned by the outer circumference of the jig container space and communicate at the tip portion of the core cylinder, and one or more slots which communicate with the jig container space and have openings on the circumference of the core cylinder. Each of the one or more slide cores is respectively inserted into each of the one or more slots allowing the slide in the radial direction of the core cylinder to form the communicating groove. The jig container space contains a slide core operating jig which is in engagement with the slide cores, and the slide cores are moved to the position where the slide cores protrude from the circumference of the core cylinder and the position where the slice cores are immersive in the circumference of the core cylinder by moving the slide core operating jig forward and backward in the axial direction of the core cylinder.

A two medical agent mixing type syringe with a communicating groove for mixing two medical agents on the inner circumference is injection-molded by moving the slide core operating jig in the axial direction of the core cylinder to protrude the slide cores from the circumference of the core cylinder and then injecting melting resin into a cavity space around the core cylinder while cooling the core cylinder by coolant.

The coolant outward and the coolant homeward can be positioned close to the cavity space because the coolant outward and the coolant homeward are partitioned by the circumference of the jig container space of the core cylinder. A sufficient coolant circulation flow is realized because the cross sectional area of the coolant outward and homeward can be made enough large.

When the core cylinder has plural slots, the slots can be formed on the circumference of the core cylinder at regular angle intervals, each of the slide cores is respectively inserted into each of the slots, and the slide cores are in engagement with the slide core operating jig.

The slide core operating jig can be made in the form of a bar shape (a flat plate with a sword-shaped tip) with one or more oblique lines which are in engagement with one or more slide cores via a dovetail groove mechanism. In this case, a combination of a slide core operating jig with a croze and a slide core with a dovetail tenon or the alternative combination of a slide core operating jig with a dovetail tenon and a slide core with a croze can be used.

The slide core operating jig can be formed by a shape-retentive wire rod with an oblique line which is in engagement with the slide core allowing the slide. The wire rod can be made by folding a metal wire like a piano wire to form the folded portion in a sword shape.

BRIEF DESCRIPTION OF DRAWINGS

FIG. 10 (A) shows a longitudinal cross-sectional view of another embodiment of a slide core operating jig when the slide cores are in the protruding position, (B) shows the slide cores mounted on the folded wire rod.

EFFECT OF INVENTION

In a syringe mold according to the present invention, the coolant flow can be sufficient by positioning the coolant circulation outward and the coolant circulation homeward close to the cavity space and setting the cross-sectional area of the coolant circulation outward and the coolant circulation homeward enough large. It is realized because the coolant circulation outward and the coolant circulation homeward are partitioned by the circumference of the jig container space in the core cylinder.

BEST MODE FOR CARRYING OUT THE INVENTION

A syringe mold according to the best mode of the present invention will be described referring to drawings. Same reference numerals will be given to the identical or similar elements and the duplicative explanation will be omitted.

Figure 1:
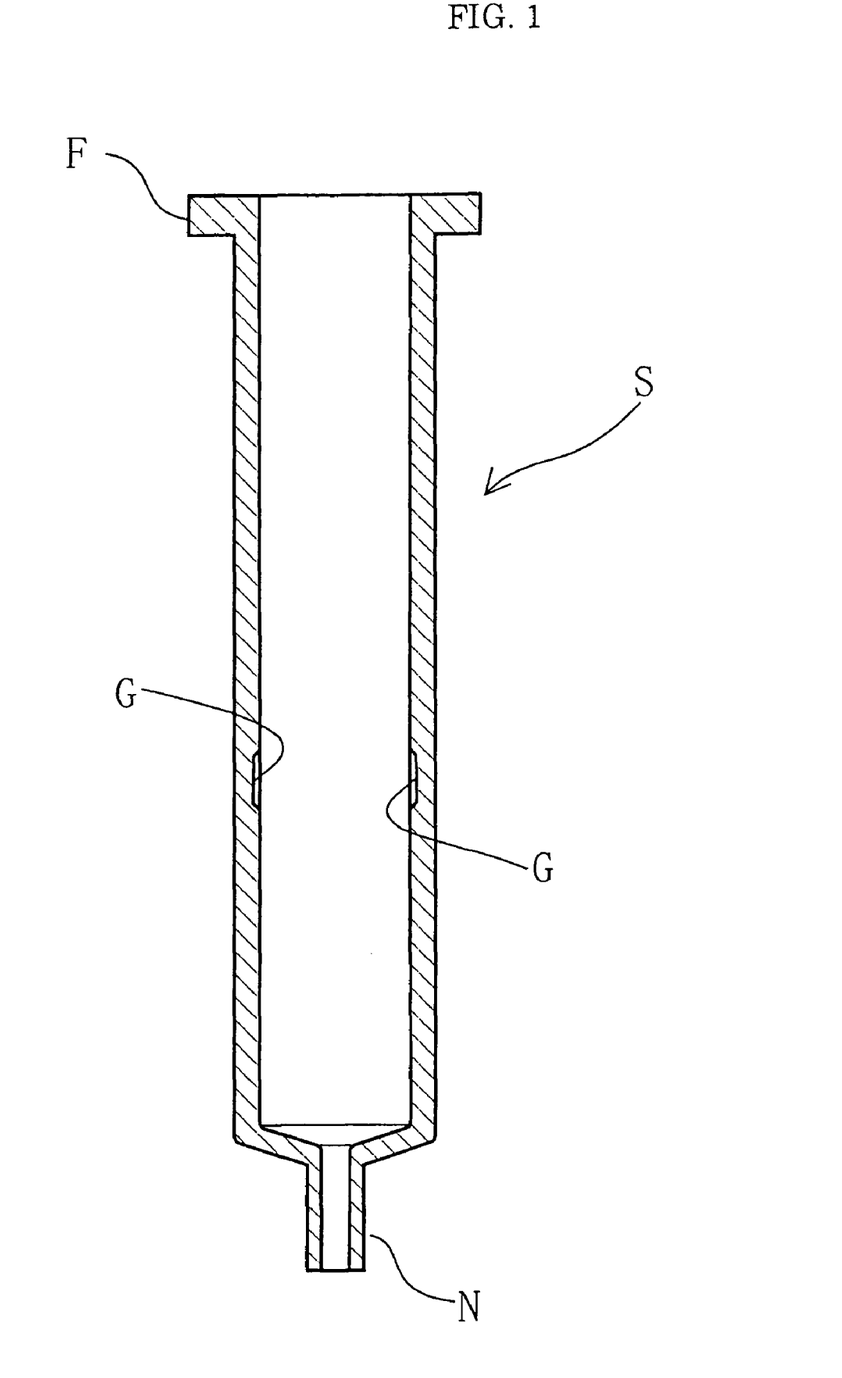
FIG. 1 shows a longitudinal cross-sectional view of a syringe which is injection-molded by a syringe mold according to one embodiment of the present invention.
Figure 2:
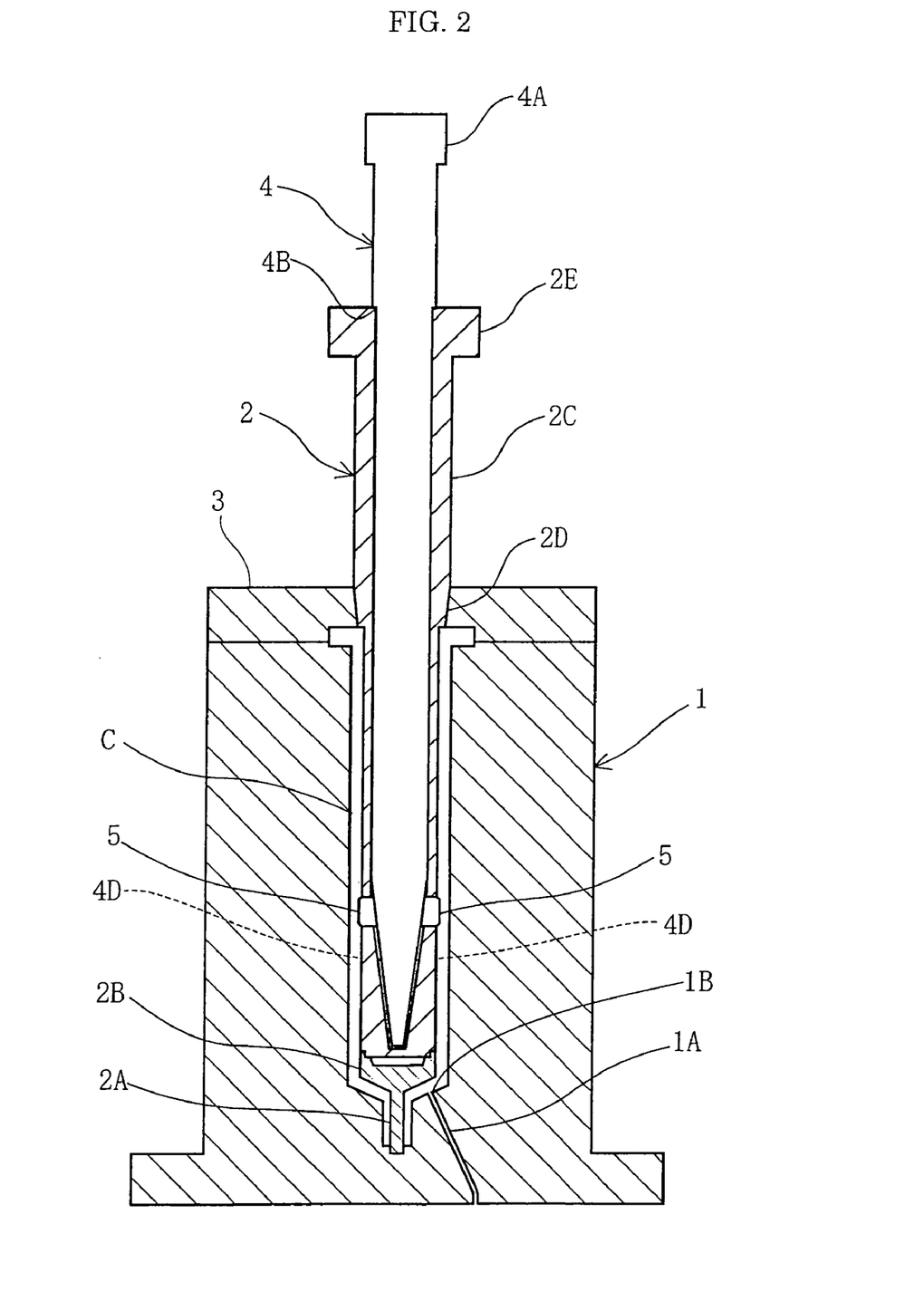
FIG. 2 shows a cross-sectional view of a schematic structure of the syringe mold for the syringe shown in FIG. 1.

FIG. 1 shows a longitudinal cross-sectional view of a syringe which is injection-molded by the syringe mold according to one embodiment of the present invention. FIG. 2 shows a cross-sectional view of a syringe mold shown in FIG. 1. One embodiment of a syringe mold according to the present invention is a syringe mold for injection-molding the syringe S for mixing two medical agents shown in FIG. 1, that is to say, the syringe S has a flange portion F at the base portion, a nozzle portion N at the tip portion and a communicating groove G for mixing two medical agents formed on the inner circumference.

As shown in FIG. 2, the syringe mold comprises a female die 1 for forming the outer circumference including a nozzle part N of the syringe S, a core cylinder 2 for forming the inner circumference of the flange S and a core plate 3 for forming the flange F of the syringe S by cooperating with the female die 1.

One end face of the female die 1 is mounted on a fixed side mounting plate (not shown in the drawing). The nozzle portion N of the syringe S is molded at the one end face. A runner 1A and a gate 1B communicating to a spool (not shown) as a passage of melting resin are formed at the one end face of the female die 1.

The core plate 3 is connected to a movable side template through a connecting member (not shown) so that the core plate takes two positions, i.e. the mold clamping position when the core plate is in close contact with the other end face of the female die, and the mold opening position when the core plate is apart from the other end face of the female die.

The core cylinder 2 has a stepped columnar outer shape penetrating the core plate 3. A cap 2B having a pin portion 2A is formed at the tip portion of the core cylinder 2 and forms the inner circumference of the nozzle portion N of the syringe S.

These portions may be made in an integrated fashion as one component or integrally-welded after these portions are made as separate components. A taper portion 2D continuing to the stepped portion is formed at the large diameter portion 2C of the core cylinder 2. A flange portion 2E is formed at the base portion of the large diameter portion 2C.

The flange potion 2E of the core cylinder 2 is connected to a movable member (not shown) so that the core cylinder takes two positions, i.e. the mold clamping position when the core cylinder is inserted into the female die 1 by penetrating the core plate 3, and the mold opening position when the core cylinder is pulled off the female die 1.

The taper portion 2D is fitted to the taper portion of the core plate 3 at the mold clamping position when the core cylinder 2 is inserted into the female die 1.

Figure 3:
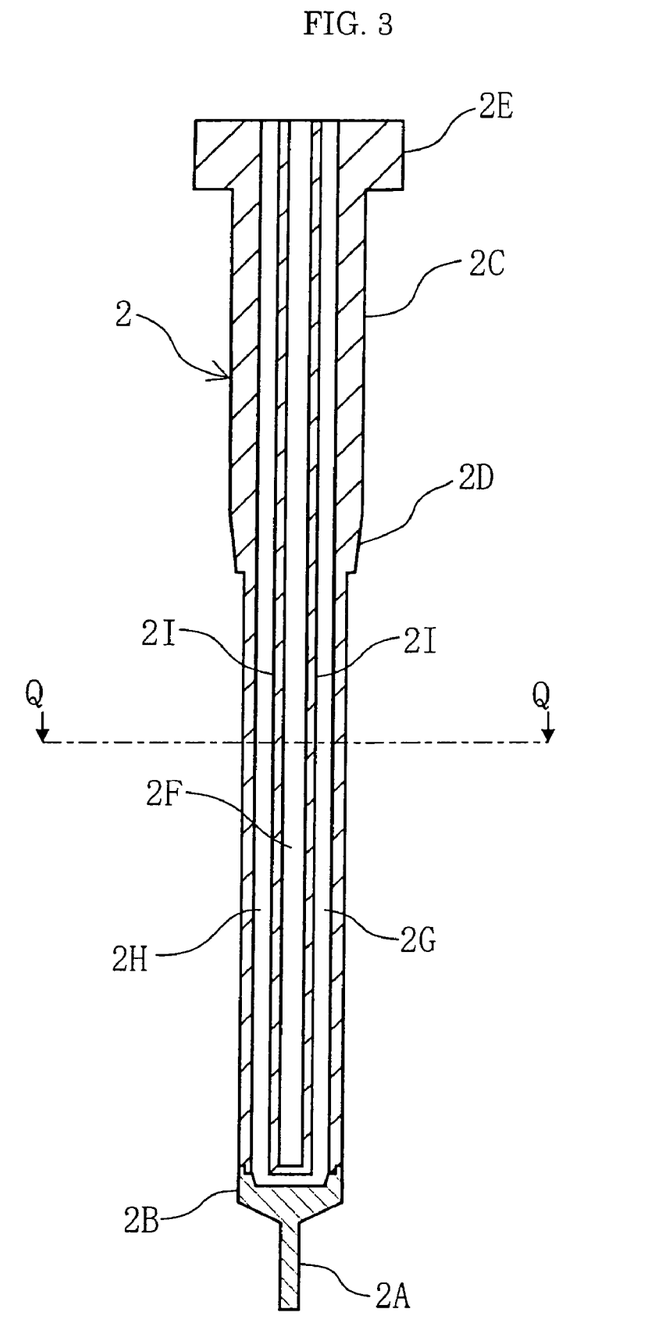
FIG. 3 shows a longitudinal cross-sectional view of the core cylinder shown in FIG. 2.
Figure 4:
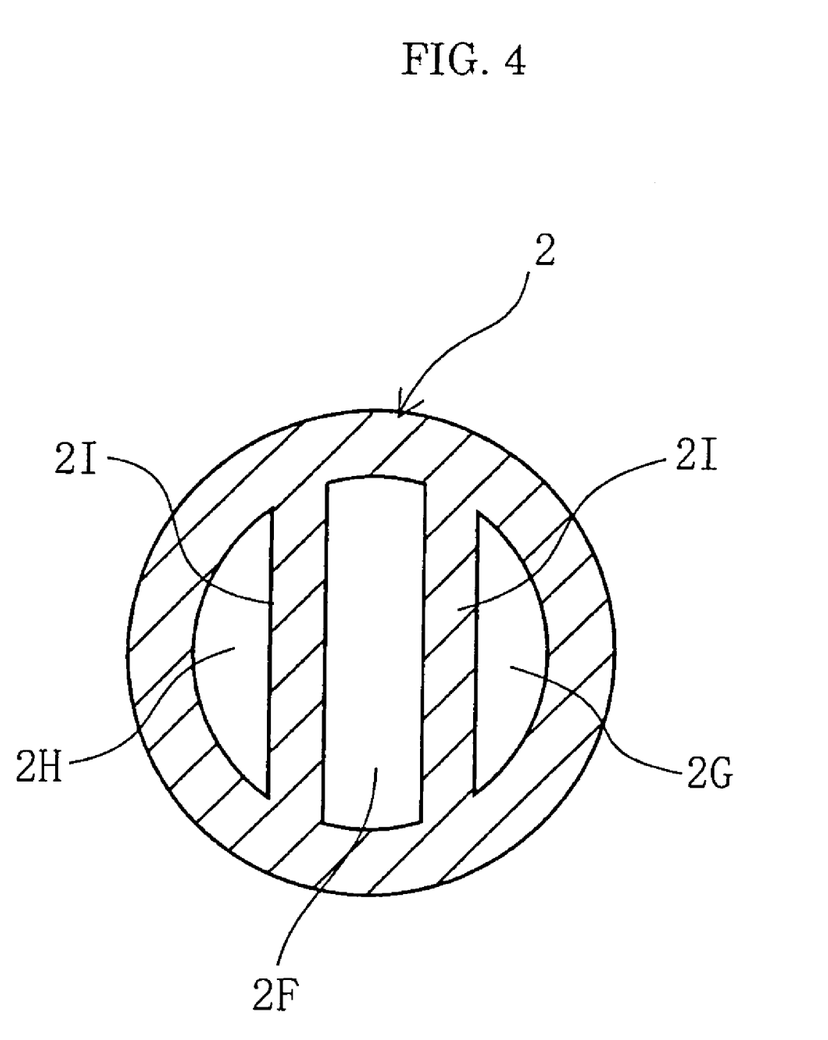
FIG. 4 shows a cross-sectional view of the core cylinder at the Q-Q line in FIG. 3.

As shown in FIG. 3 and FIG. 4 (a cross-sectional view of the core cylinder at Q-Q line in FIG. 3), the core cylinder 2 has a jig container space 2F extending axially, and a coolant circulation outward 2G and a coolant circulation homeward 2H which are partitioned by the circumference of the jig container space 2F and communicate at the cap 2B of the tip portion inside the core cylinder 2. The coolant circulation outward 2G and the coolant circulation homeward 2H are partitioned by a pair of bulkheads 2I, 2I which partition the inner space of the core cylinder 2 in the cross-sectional direction and continue at the tip portion inside the core cylinder 2. The coolant circulation outward 2G and the coolant circulation homeward 2H are formed on both sides of the jig container space 2F in the middle of the 2.

Figure 5:
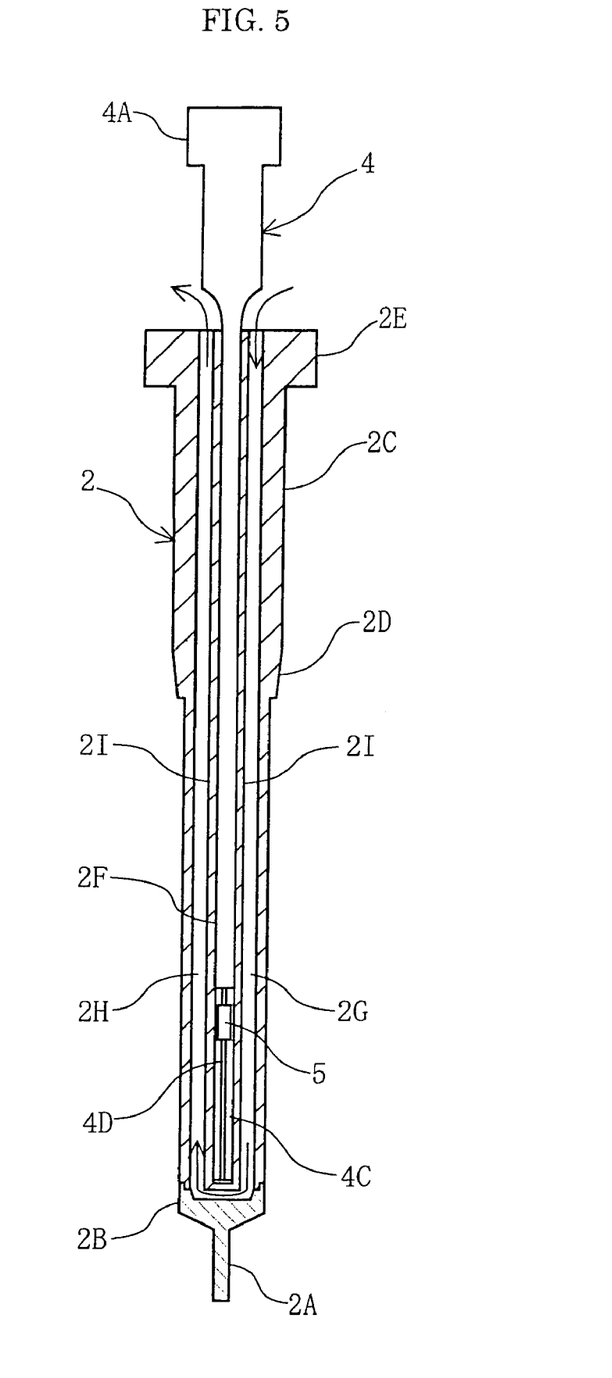
FIG. 5 shows a longitudinal cross-sectional view of the core cylinder shown in FIG. 3 when the slide core operating jig is inserted.
Figure 6:
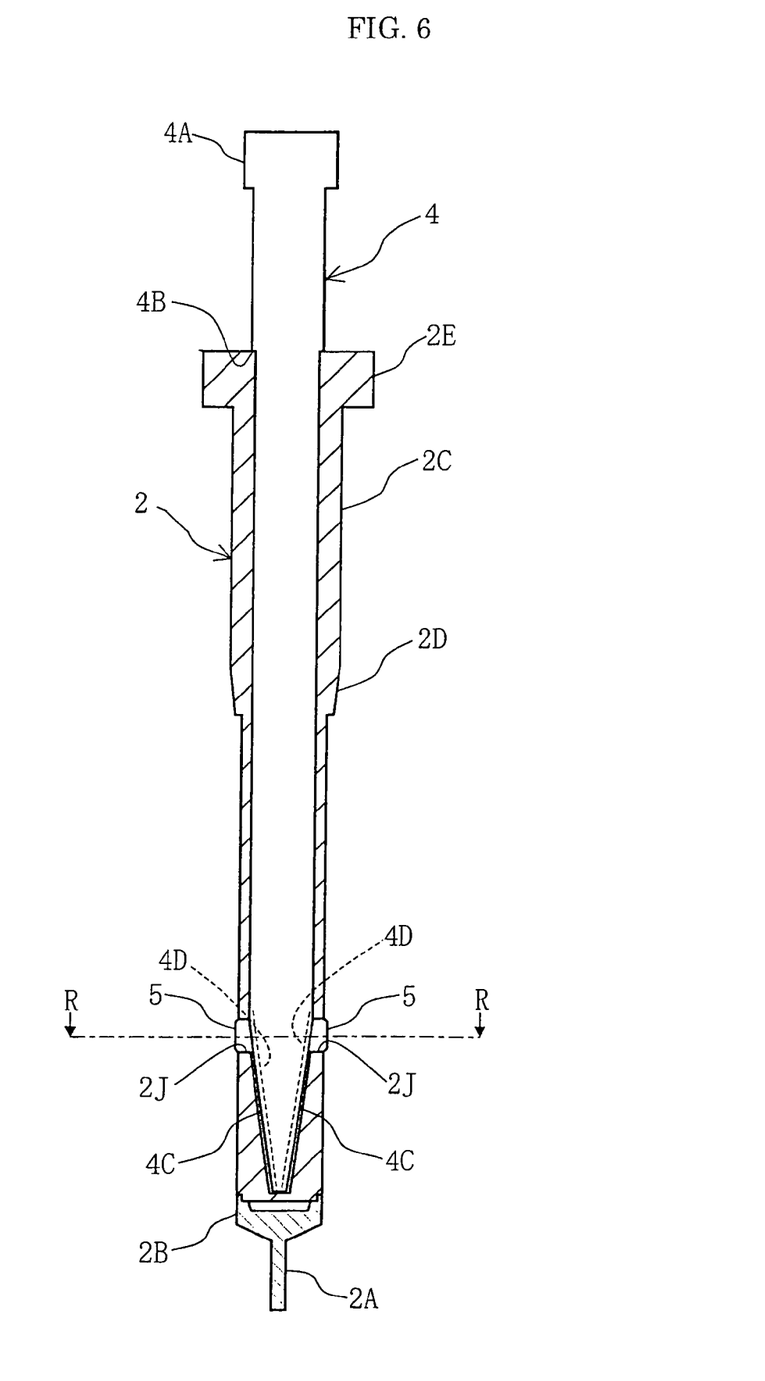
FIG. 6 shows a longitudinal cross-sectional view of the core cylinder shown in FIG. 2 when the slide core operating jig is inserted.
Figure 7:
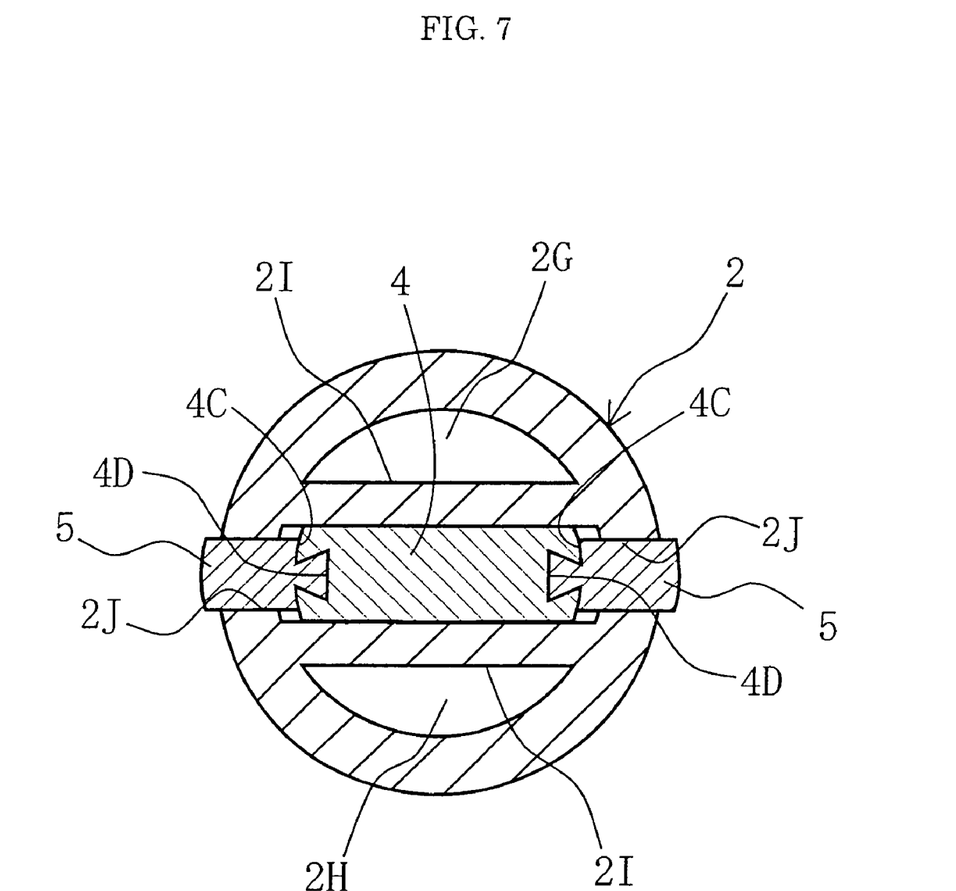
FIG. 7 shows a cross-sectional view of the core cylinder at the R-R line in FIG. 6.

As shown in FIG. 5 and FIG. 6, the jig container space 2F in the core cylinder 2 contains a flat bar-shaped slide core operating jig 4 with a sword point shaped tip. The slide core operating jig 4 has a head 4A for forward and backward operation at the rear anchor portion and a stopper stepped portion 4B for contacting a flange portion 2E of the core cylinder 2 on the lower side. Crozes 4D, 4D are formed on the oblique lines 4C, 4C on the both sides of the sword point shaped tip of the slide core operating jig 4. A pair of slide cores 5, 5 is in engagement with the crozes 4D, 4D via dovetail tenons (see FIG. 7), A pair of slide cores 5, 5 forms communicating grooves G, G in the syringe shown in FIG. 1. The slide cores 5, 5 are inserted into a pair of slots 2J, 2J allowing the slide in the radial direction as shown in FIG. 7 (a cross sectional view of the core cylinder on R-R line in FIG. 6. A pair of slots 2J, 2J penetrates the core cylinder 2 in the radial direction to communicate with the jig container space 2F and creates openings on the circumference of the core cylinder 2.

The slide cores 5, 5 move forward and backward in the radial direction of the core cylinder 2 in conjunction of the forward and backward movement of the slide core operating jig 4 in the axial direction of the core cylinder 2. When the slide core operating jig 4 is moved forward in the axial direction of the core cylinder 2, the slide cores 5, 5 are put in the position where the slide cores 5, 5 protrude from the circumference of the core cylinder 2 as shown in FIG. 6. When the slide core operating jig 4 is moved backward in the axial direction of the core cylinder 2, the slide cores 5, 5 are put in the position where the slide cores 5, 5 are immersive in the circumference of the core cylinder 2 as shown in FIG. 8.

A process for injection-molding a syringe S having communicating grooves G, G on the inner circumference of a two medical agent mixing type syringe by using a syringe mold according to one embodiment of the present invention will be described. As shown in FIG. 2, the core cylinder 2 is put in the mold clamping condition where a cavity space C is formed around the core cylinder 2 by moving the slide core operating jig 4 forward toward the tip side in the axial direction of the core cylinder 2 so that the slide cores 5, 5 protrude from the circumference of the core cylinder 2 as shown in FIG. 6. The spool (not shown) fills melting resin in the cavity space C between the cavity space of the female die 1 and the outer circumference of the core cylinder 2 through the runner 1A and gate 1B shown in FIG. 2 while cooing the core cylinder 2 by circulating the coolant from the coolant circulation outward 2G to the coolant circulation homeward 2H sown in FIG. 5. The melting resin filled in the cavity space C is solidified by cooling the core cylinder 2 through continuous circulation of the coolant.

Figure 8:
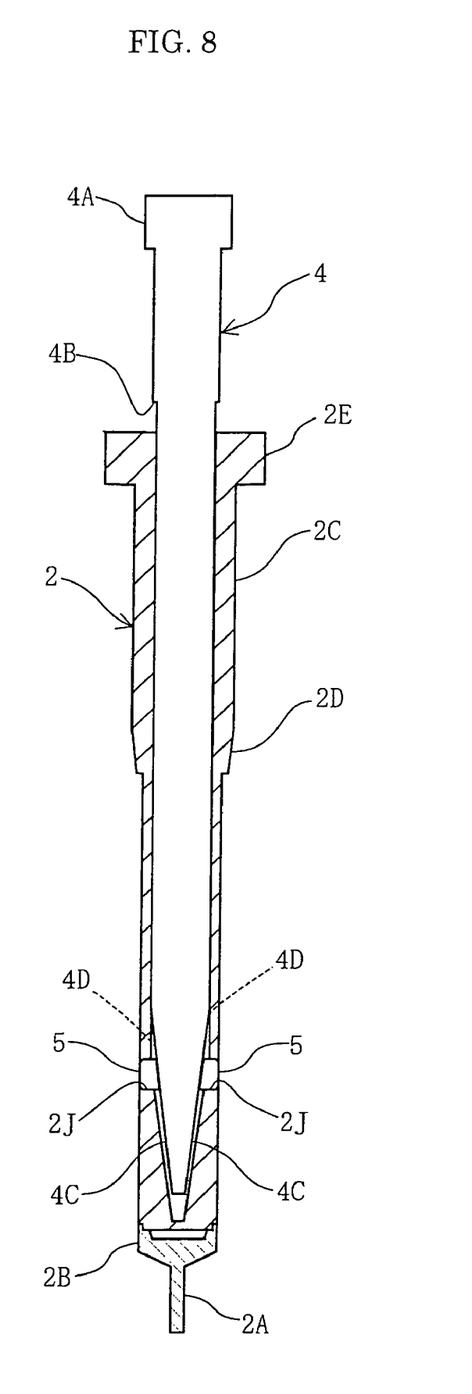
FIG. 8 shows a cross-sectional view of the core cylinder when the slide core operating jig is moved backward.

The slide core operating jig 4 is moved backward toward the rear anchor side in the axial direction of the core cylinder 2 and put in the position where the slide cores 5, 5 are immersive in the circumference of the core cylinder 2 as shown in FIG. 8. After putting the syringe mold in the mold opening condition, the core cylinder 2 and the injection-molded syringe S (see FIG. 1) are pulled out from the female die 1, and then the syringe S is separated from the core cylinder 2.

The coolant flow can be sufficient by positioning the coolant circulation outward 2G and the coolant circulation homeward 2H close to the cavity space and setting the cross-sectional area of the coolant circulation outward 2G and the coolant circulation homeward 2H enough large because the coolant circulation outward 2G and the coolant circulation homeward 2H are partitioned by the circumference of the jig container space 2F in the core cylinder 2. It is possible to prevent molding failure due to the insufficient cooling of molding male die (core cylinder) by using the syringe mold according to this embodiment.

Figure 9:
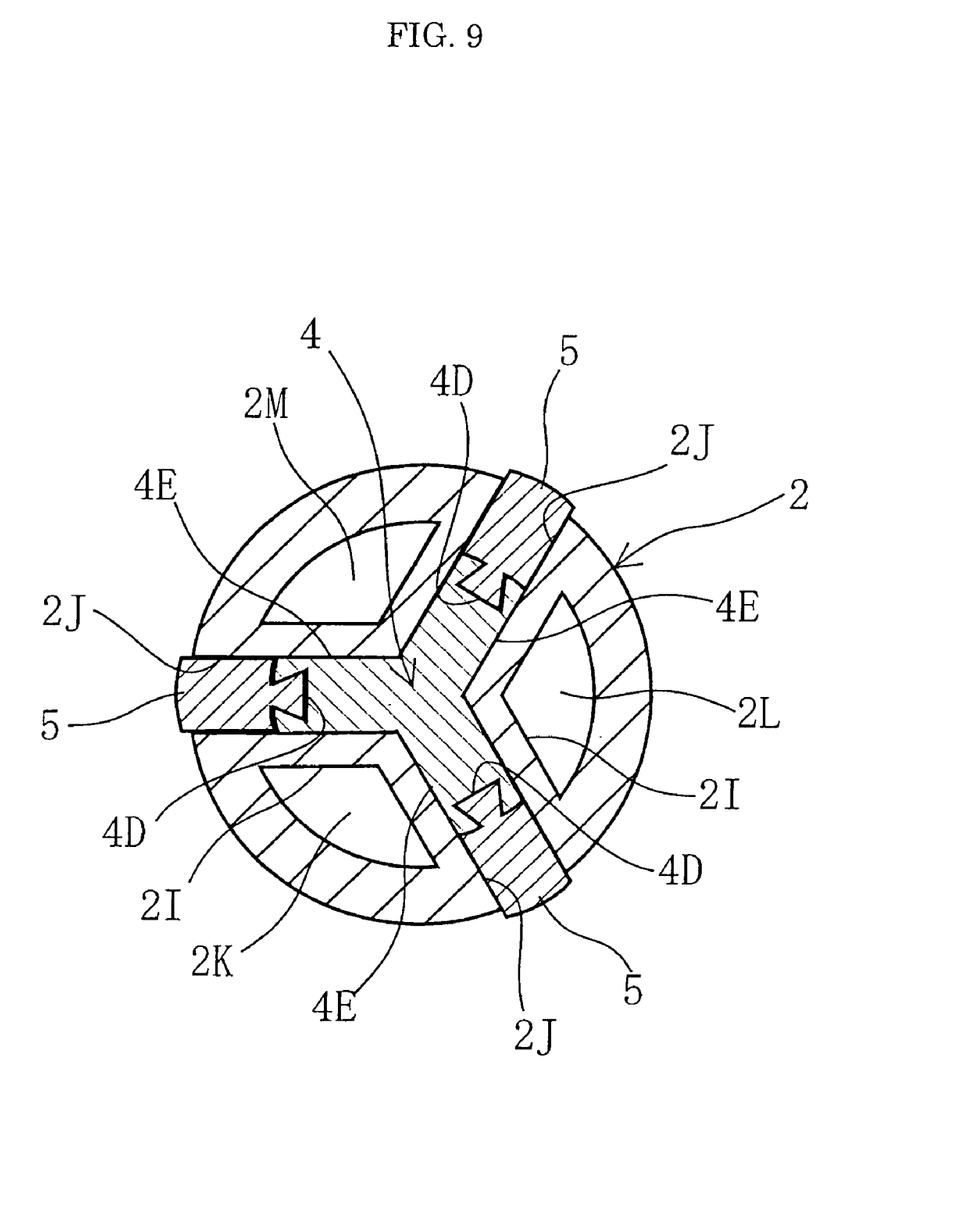
FIG. 9 shows a cross-sectional view of a modified example of the slide core operating jig.

The scope of the present invention should not be construed to limit to the aforementioned embodiment. For example, the syringe mold can have only one slide core 5 on one side instead of a pair of slide cores. The slide core operating jig 4 may have the cross-sectional shape shown in FIG. 9, that is to say, three protruding ribs 4E are circumferentially positioned at regular angle intervals instead of the bar-shaped slide core operating jig 4 with the sword-shaped tip portion. In this case, crozes 4D, 4D, 4D are formed on the protruding end face of each of the ribs 4E, E, 4E, and each of three slide cores 5, 5, 5 is in engagement with each of the crozes 4D, 4D, 4D respectively through dovetail tenons.

Three slots 2J, 2J, 2J are circumferentially positioned on the core cylinder 2 at regular angle intervals. Each of the slide cores 5, 5, 5 is inserted allowing the slide in the radial direction of the core cylinder 2. The bulkheads 2I, 2I, 2I have a cross sectional shape which corresponds to three ribs 4E, 4E, 4E, and the bulkheads 2I, 2I, 2I partition the space around the jig container space (not shown) and three coolant flow passages 2K, 2L, 2M are formed as the circulation outward and homeward. The syringe mold with the slide core operating jig 4 having the cross-sectional shape shown in FIG. 9 can exert an effect which is similar to that of the aforementioned syringe mold.

The slide core operating jig 4 can be formed by a folded wire rod instead of the bar-shaped jig shown in FIG. 5 and FIG. 6. The tip portion with a sword shaped oblique lines can be formed by folding a shape-retentive wire rod like a piano wire. That is to say, the folded wire rod can have a planar shape with a sword-shaped folded portion.

Figure 10A:
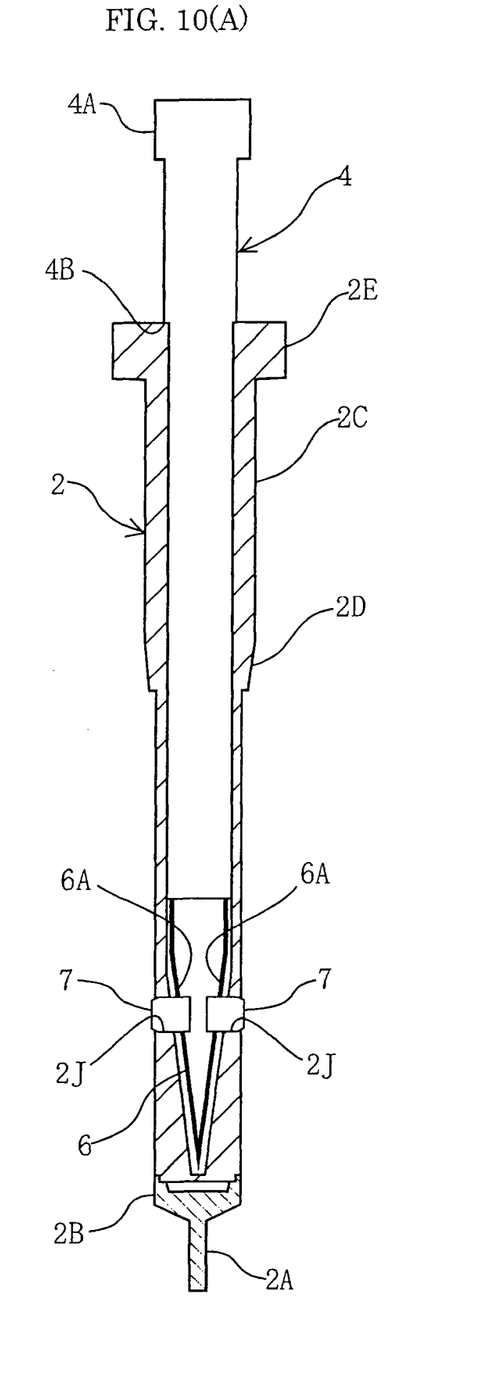
Figure 10B:
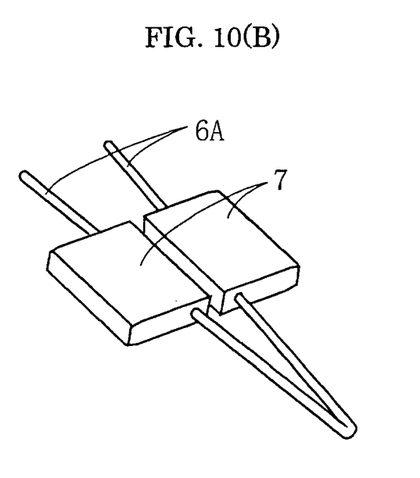
Figure 11:
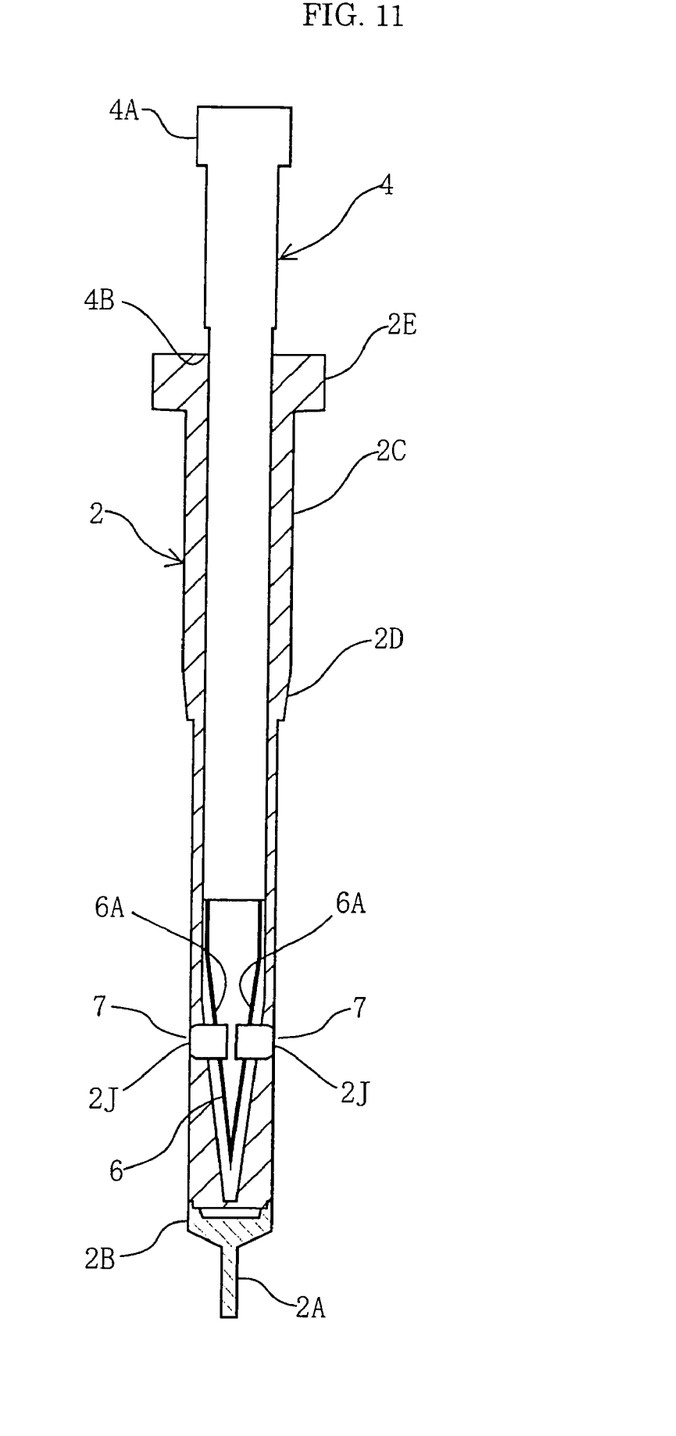
FIG. 11 shows the embodiment of FIG. 10(A) when the slide cores 7 are in the immersive condition.

FIGS. 10 (A), (B) and FIG. 11 show one example of slide core operating jig 4 with a sword-shaped tip portion formed by a folded wire rod 6. FIG. 10 (A) shows the condition when the slide cores 7, 7 are in the protruding position. FIG. 10(B) shows the condition when the slide cores are attached to the folded wire rod 6.

FIG. 11 shows the condition when the slide cores 7, 7 are in the immersive position. In FIG. 10 (A) and FIG. 11, the rear anchor portion of the folded wire rod 6 is firmly fixed to the slide core operating jig 4 by an appropriate means like welding. As shown in FIG. 10(B), the slide cores 7, 7 have filling holes at their rear anchor portions, and the oblique portions 6A, 6A of the folded wire rod 6 are inserted in the fitting holes allowing the slide.

The syringe mold having the slide core operating jig 4 with the folded wire rod 6 shown in FIG. 10(A) and FIG. 11 exerts an effect similar to that of the aforementioned embodiment. The female die 1 shown in FIG. 2 can be either separable or integrated.

The invention claimed is:

1. A syringe mold including a core cylinder for forming the inner circumference of a syringe having a communicating groove for mixing two medical agents, wherein the core cylinder comprises a jig container space extending axially, a coolant circulation outward and a coolant circulation homeward which are partitioned by the outer circumference of the jig container space and communicate at the tip portion of the core cylinder, and one or more slots which communicate with the jig container space and have openings on the circumference of the core cylinder, the one or more slide cores are respectively inserted into the one or more slots allowing the slide in the radial direction of the core cylinder to form the communicating groove, the jig container space contains a slide core operating jig which is in engagement with the slide cores, and the slide cores are put in the position where the slide cores protrude from the circumference of the core cylinder and the position where the slide cores are immersive in the circumference of the core cylinder by moving the slide core operating jig forward and backward in the axial direction of the core cylinder.

2. A syringe mold according to claim 1, wherein the core cylinder has plural slots which are formed on the circumference of the core cylinder at regular angle intervals, each of the slide cores are respectively inserted into each of the slots, and the slide cores are in engagement with the slide core operating jig.

3. A syringe mold according to claim 1, wherein the slide core operating jig is made in a bar shape with one or more oblique lines which are in engagement with one or more slide cores through a dovetail groove mechanism.

4. A syringe mold according to claim 1, wherein the slide core operating jig is formed by a shape-retentive wire rod with an oblique line which is in engagement with the slide core allowing the slide.

5. A syringe mold according to claim 2, wherein the slide core operating jig is made in a bar shape with one or more oblique lines which are in engagement with one or more slide cores through a dovetail groove mechanism.

6. A syringe mold according to claim 2, wherein the slide core operating jig is formed by a shape-retentive wire rod with an oblique line which is in engagement with the slide core allowing the slide.

* * * * *